(12) United States Patent
Karls et al.

(10) Patent No.: US 10,098,980 B2
(45) Date of Patent: Oct. 16, 2018

(54) MULTI-LAYER ARTICLES

(71) Applicant: 3M INNOVATIVE PROPERTIES COMPANY, St. Paul, MN (US)

(72) Inventors: Korey W. Karls, Coon Rapids, MN (US); Matthew T. Scholz, Woodbury, MN (US); Jeffrey O. Emslander, Stillwater, MN (US); Amy S Determan, Mahtomedi, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 438 days.

(21) Appl. No.: 14/433,884

(22) PCT Filed: Oct. 11, 2013

(86) PCT No.: PCT/US2013/064481
§ 371 (c)(1),
(2) Date: Apr. 7, 2015

(87) PCT Pub. No.: WO2014/059239
PCT Pub. Date: Apr. 17, 2014

(65) Prior Publication Data
US 2015/0283285 A1    Oct. 8, 2015

Related U.S. Application Data

(60) Provisional application No. 61/713,107, filed on Oct. 12, 2012.

(51) Int. Cl.
*B32B 27/08*    (2006.01)
*A61L 15/24*    (2006.01)
(Continued)

(52) U.S. Cl.
CPC ............ *A61L 15/24* (2013.01); *A61F 13/022* (2013.01); *A61F 13/0206* (2013.01);
(Continued)

(58) Field of Classification Search
CPC ........... B32B 5/022; B32B 5/24; B32B 27/08; B32B 27/12; B32B 2307/7265; B32B 2535/00; Y10T 442/671; Y10T 442/678
See application file for complete search history.

(56) References Cited

U.S. PATENT DOCUMENTS

| 1,975,504 A | 10/1934 | Formhals |
| 3,565,985 A | 2/1971 | Schrenk et al. |

(Continued)

FOREIGN PATENT DOCUMENTS

| DE | 199 29 709 | 12/2000 |
| EP | 0 505 027 | 9/1992 |

(Continued)

OTHER PUBLICATIONS

Kurarity, A Novel Acrylic Block Copolymer, published by Kuraray Co., Ltd. (2014), available at https://www.elastomer.kuraray.com/fileadmin/user_upload/ELASTOMERE/DOWNLOADS/product_brochures/KURARITY.pdf.*

(Continued)

*Primary Examiner* — Jeremy R Pierce
(74) *Attorney, Agent, or Firm* — Pamela L. Stewart; Melanie G. Gover; James A. Baker (57) ABSTRACT

Multilayer articles having an absorbent nonwoven layer and a barrier layer are described, including those having a surfactant-treated, aliphatic polyester, nonwoven absorbent layer and a barrier layer. Multilayer articles including a tie layer used to enhance the bond between the hydrophilic absorbent layer and the barrier layer are also described. Methods of making and using such articles are also described.

24 Claims, 1 Drawing Sheet

(51) Int. Cl.
| | | |
|---|---|---|
| A61L 15/48 | (2006.01) | |
| A61L 31/14 | (2006.01) | |
| A61L 15/42 | (2006.01) | |
| B32B 5/02 | (2006.01) | |
| B32B 5/24 | (2006.01) | |
| B32B 27/12 | (2006.01) | |
| A61F 13/02 | (2006.01) | |
| D04H 1/435 | (2012.01) | |

(52) U.S. Cl.
CPC ............... *A61L 15/42* (2013.01); *A61L 15/48* (2013.01); *A61L 31/14* (2013.01); *B32B 5/022* (2013.01); *B32B 5/24* (2013.01); *B32B 27/08* (2013.01); *B32B 27/12* (2013.01); *D04H 1/435* (2013.01); *B32B 2262/0276* (2013.01); *B32B 2307/7265* (2013.01); *B32B 2535/00* (2013.01); *Y10T 442/671* (2015.04); *Y10T 442/678* (2015.04)

(56) References Cited

U.S. PATENT DOCUMENTS

| | | | |
|---|---|---|---|
| 3,849,241 A | 11/1974 | Butlin et al. | |
| 3,874,886 A | 4/1975 | Levecque et al. | |
| 4,118,531 A | 10/1978 | Hauser | |
| 4,363,646 A | 12/1982 | Torobin | |
| 4,536,361 A | 8/1985 | Torobin | |
| 4,744,365 A | 5/1988 | Kaplan et al. | |
| 4,977,892 A | 12/1990 | Ewall | |
| 5,227,107 A | 7/1993 | Dickenson et al. | |
| 5,427,842 A | 6/1995 | Bland et al. | |
| 5,475,063 A | 12/1995 | Kaplan et al. | |
| 5,496,507 A | 3/1996 | Angadjivand et al. | |
| 5,589,122 A | 12/1996 | Leonard et al. | |
| 5,599,602 A | 2/1997 | Leonard et al. | |
| 5,660,922 A | 8/1997 | Herridge et al. | |
| 5,883,199 A | 3/1999 | McCarthy et al. | |
| 5,901,706 A | 5/1999 | Griesbach et al. | |
| 5,910,368 A | 6/1999 | Ehret | |
| 5,952,433 A | 9/1999 | Wang et al. | |
| 5,997,568 A | 12/1999 | Liu | |
| 6,075,118 A | 6/2000 | Wang et al. | |
| 6,093,792 A | 7/2000 | Gross et al. | |
| 6,111,060 A | 8/2000 | Gruber et al. | |
| 6,114,017 A | 9/2000 | Fabbricante et la. | |
| 6,117,928 A | 9/2000 | Hiltunen et al. | |
| 6,143,863 A | 11/2000 | Gruber et al. | |
| 6,183,670 B1 | 2/2001 | Torobin et al. | |
| 6,225,388 B1* | 5/2001 | Tsai | A61F 13/15252 428/401 |
| 6,315,806 B1 | 11/2001 | Torobin et al. | |
| 6,352,948 B1* | 3/2002 | Pike | B32B 5/02 442/361 |
| 6,382,526 B1 | 5/2002 | Reneker et al. | |
| 6,461,716 B1* | 10/2002 | Lee | A61F 13/512 428/132 |
| 6,645,618 B2 | 11/2003 | Hobbs et al. | |
| 6,743,273 B2 | 6/2004 | Chung et al. | |
| 6,764,566 B1 | 7/2004 | Griesbach, III et al. | |
| 6,800,226 B1 | 10/2004 | Gerking | |
| 6,861,025 B2 | 3/2005 | Erickson et al. | |
| 7,241,838 B2 | 7/2007 | Shelby et al. | |
| 8,858,986 B2 | 10/2014 | Scholz et al. | |
| 2003/0040691 A1 | 2/2003 | Griesbach et al. | |
| 2003/0191243 A1* | 10/2003 | Hamada | C08F 297/026 525/94 |
| 2003/0228442 A1 | 12/2003 | Price et al. | |
| 2004/0243080 A1 | 12/2004 | Baer | |
| 2005/0249791 A1 | 11/2005 | Hobbs et al. | |
| 2006/0041239 A1* | 2/2006 | Nagahara | A61F 13/15203 604/380 |
| 2008/0038976 A1 | 2/2008 | Berrigan et al. | |
| 2008/0058450 A1* | 3/2008 | Stimpson | C08K 5/12 524/296 |
| 2008/0142023 A1 | 6/2008 | Schmid et al. | |
| 2008/0160861 A1 | 7/2008 | Berrigan et al. | |
| 2008/0200890 A1* | 8/2008 | Wood | A01N 25/10 604/360 |
| 2009/0264844 A1* | 10/2009 | Autran | A61F 13/15593 604/365 |
| 2011/0151737 A1 | 6/2011 | Moore et al. | |

FOREIGN PATENT DOCUMENTS

| | | |
|---|---|---|
| JP | S62-122752 A | 6/1987 |
| JP | 7-507847 | 8/1995 |
| JP | 2000-517225 | 12/2000 |
| JP | 2003-514136 | 4/2003 |
| WO | WO 84/04311 | 11/1984 |
| WO | WO 1993/25746 | 12/1993 |
| WO | WO 94/07941 | 4/1994 |
| WO | WO 94/07949 | 4/1994 |
| WO | WO 96/22330 | 7/1996 |
| WO | WO 1998/09589 | 3/1998 |
| WO | WO 98/24951 | 6/1998 |
| WO | WO 98/50611 | 11/1998 |
| WO | WO 99/06456 | 2/1999 |
| WO | WO 99/50345 | 10/1999 |
| WO | WO 00/12606 | 3/2000 |
| WO | WO 2001/34886 | 5/2001 |
| WO | WO 02/47737 | 6/2002 |
| WO | WO 02/094330 | 11/2002 |
| WO | WO 2005/016197 | 2/2005 |
| WO | WO 2009/152345 | 12/2009 |

OTHER PUBLICATIONS

Gedde, U.W.; Polymer Physics; 1st Ed.; Chapman & Hall; (1995); p. 298 (7 pgs.).

Kricheldorf, H.R.; "Syntheses and application of polylactides", *Chemosphere*, vol. 43; 2001; pp. 49-54.

Leenslag, J.W. et al., "Resorbable Materials of Poly(L-lactide). V. Influence of Secondary Structure on the Mechanical Properties and Hyrdolyzability of Poly(L-lactide) Fibers Produced by a Dry-Spinning Method"; *Journal of Applied Polymer Science*; vol. 29, 1984; pp. 2829-2842.

Satas, D.; Handbook of Pressure Sensitive Adhesive Technology, Second Edition, (1989) Van Nostrand Reinhold (9 pgs.).

Tsuji, H. et al.; Sterocomplex formation between enantiomeric poly(lactic acid)s. XI. Mechanical properties and morphology of solution-cast films; *Polymer*; vol. 40; 1999; pp. 6699-6708.

Wente, V.A.; "Superfine Thermoplastic Fibers", Industrial Engineering Chemistry, vol. 48, No. 8, (1956); pp. 1342-1346.

Ziabicki, A.; Fundamentals of Fibre Formation—The Science of Fibre Spinning and Drawing, (1976) A Wiley-Interscience Publication; John Wiley & Sons (3 pgs).

* cited by examiner

MULTI-LAYER ARTICLES

CROSS REFERENCE TO RELATED APPLICATIONS

This application is a national stage filing under 35 U.S.C. 371 of PCT/US2013/064481, filed Oct. 11, 2013, which claims priority to U.S. Provisional Patent Application No. 61/713,107, filed Oct. 12, 2012, the disclosure of which is incorporated by reference in its entirety herein.

FIELD

The present disclosure relates to multilayer articles having an absorbent nonwoven layer and a polyolefin barrier layer. The present disclosure also relates to multilayer articles including a tie layer; specifically tie layers used to enhance the bond between a hydrophilic absorbent layer and a polyolefin barrier layer. Methods of making and using such articles are also described.

SUMMARY

Briefly, in one aspect, the present disclosure provides a multilayer article comprising a hydrophilic absorbent layer, a polyolefin barrier layer, and a tie layer bonding the absorbent layer to the barrier layer. The absorbent layer comprises a nonwoven web of fibers comprising an aliphatic polyester combined with a surfactant.

In another aspect, the present disclosure provides a multilayer article comprising an absorbent layer comprising a hydrophilic first ply and a second ply, and a polyolefin barrier layer bonded to the second ply. The first ply comprises a first nonwoven web of fibers comprising an aliphatic polyester combined with a surfactant and the second ply comprises a second nonwoven web of fibers comprising the aliphatic polyester. In some embodiments, the barrier layer is directly bonded to the second ply. In some embodiments, the barrier layer is indirectly bonded to the second ply; wherein the multilayer article further comprises a tie layer positioned between and bonded to the barrier layer and the second ply.

In some embodiments, the tie layer comprises a copolymer of at least one olefin monomer and at least one polar monomer. In some embodiments, the copolymer further comprises at least one reactive monomer, wherein the reactive monomer comprises a reactive group that covalently reacts with a hydroxyl group. In some embodiments, the tie layer further comprises a reactive polymer comprising at least one reactive monomer, wherein the reactive monomer comprises a reactive group that covalently reacts with a hydroxyl group. In some embodiments, the tie layer further comprises a tackifier.

In some embodiments, at least one olefin monomer is ethylene. In some embodiments, at least one polar monomer is selected from the group consisting of vinyl acetate, a C1 to C8 acrylate, a C1 to C4 acrylic acid, and combinations thereof. In some embodiments, the reactive group of the reactive monomer is an anhydride group or an epoxy group. In some embodiments, the tie layer includes a thermoplastic elastomer. In some embodiments, the thermoplastic elastomer is a block copolymer comprising alkyl methacrylate and alkyl acrylate blocks, e.g., a poly(methyl methacrylate)-poly(butyl acrylate)-poly(methyl methacrylate) copolymer. In some embodiments, the tie layer further comprises an alkyl benzoate plasticizer.

In some embodiments, the aliphatic polyester comprises poly(lactic acid). In some embodiments, the surfactant comprises at least one of an anionic surfactant and a nonionic polyethoxylated surfactant. In some embodiments, the absorbent layer further comprises a nonvolatile carrier blended with the aliphatic polyester and the surfactant. In some embodiments, the nonvolatile carrier comprises at least one of a polyalkylene glycol, a thermally stable polyhydric alcohol, a low molecular weight ester of a polyhydric alcohol and combinations thereof.

In some embodiments, the olefin comprises at least one of polyethylene and polypropylene. In some embodiments, the polyethylene comprises at least one of low density polyethylene and linear low density polyethylene.

The above summary of the present disclosure is not intended to describe each embodiment of the present invention. The details of one or more embodiments of the invention are also set forth in the description below. Other features, objects, and advantages of the invention will be apparent from the description and from the claims.

DETAILED DESCRIPTION

A patient's skin flora entering a surgical wound is generally recognized as the primary cause of surgical site infections. In an effort to inhibit or prevent flora present on a patient's skin from entering the wound, sterile disposable drapes are used to cover the patient during surgical procedures. Preferably, absorbent drapes are used in an effort to prevent fluids from draining into the wound, or onto operating personnel or the floor. However, absorbent layers by themselves could provide a fluid path for bacteria on the skin to pass through the drape and into the wound. Thus, drapes are often multilayer articles that may include a barrier layer to prevent skin bacteria flora from migrating from the skin, through the drape, and into the wound.

Current drapes also satisfy other criteria such as being strong (high machine and cross direction tensile strength), and having low flammability, while remaining relatively low in cost. There is a desire, however, to make a strong, fluid impervious, absorbent drape that is softer and more drapable. There is also a desire to increase the content of resource-renewable (i.e., plant derived as opposed to petroleum derived) materials in the drape as much as possible. There is a further desire to provide these and other benefits while maintaining low cost, as drapes are generally a single-use, disposable product.

Traditionally, thermoplastic polymers have been used to create layers suitable for the absorbent and barrier layers such as blown and cast films, extruded sheets, foams, fibers and products made from fibers such as woven and knitted fabrics, and non-woven fibrous webs. Traditionally, many of these layers have been made from petroleum-based thermoplastics such as polyolefins. However, there is a growing interest in replacing these petroleum-based polymers with resource renewable polymers, i.e. polymers derived from plant based materials. Ideal resource renewable polymers are "carbon dioxide neutral" meaning that as much carbon dioxide is consumed in growing the plant based material as is given off when the product is made and disposed of. Biodegradable materials have adequate properties to permit them to break down when exposed to conditions which lead to composting. Examples of materials thought to be biodegradable include aliphatic polyesters such as poly(lactic acid), poly(glycolic acid), poly(caprolactone), copolymers of lactide and glycolide, poly(ethylene succinate), polybutylene succinate), polyhydroxybutyrate, and combinations thereof.

In some embodiments, the absorbent layer of the present disclosure comprises aliphatic polyesters and/or polyamides. In some embodiments, the absorbent layer comprises fibers comprising aliphatic polyesters and/or polyamides. In some embodiments, the absorbent layer comprises a woven or nonwoven web. In some embodiments, the nonwoven web may be a melt-blown, spun-bond, spun-laced, and/or wet or dry laid.

Exemplary aliphatic thermoplastic polyesters include poly(lactic acid), poly(glycolic acid), poly(lactic-co-glycolic acid), polyhydroxybutyrate, polyhydroxyvalerate, blends, and copolymers thereof. Blends of aliphatic thermoplastic polyesters and blends of one or more aliphatic thermoplastic polyesters with one or more of a variety of other polymers including aromatic polyesters, aliphatic/aromatic copolyesters, cellulose esters, cellulose ethers, thermoplastic starches, ethylene vinyl acetate, polyvinyl alcohol, ethylenevinyl alcohol, and the like may also be used. In blended compositions that include thermoplastic polymers which are not aliphatic polyesters, the aliphatic polyester is typically present at a concentration of greater than 60% by weight of total blend, preferably at least 70%, e.g., at least 75, 80, 85, 90 and even at least 95% by weight of total blend.

These webs are generally not sufficiently water absorbent unless combined with water absorbent fibers such as cellulose, cellulose derivatives, and other polysaccharide based fibers and the like. Alternatively, or in addition to such an approach, the aliphatic polyester resin can be combined with one or more surfactants. For example, in some embodiments, surfactants may be sprayed, coated or otherwise applied to the surface of fibers comprising an aliphatic polyester. Coating methods to provide a hydrophilic surface are known, but also have some limitations. First, the extra step required in coating preparation is expensive and time consuming. Second, many of the solvents used for coating are flammable liquids or have exposure limits that require special production facilities. Third, the quantity of surfactant can also be limited by the solubility of the surfactant in the coating solvent and the thickness of the coating.

In some embodiments, aliphatic thermoplastic polyester(s) and surfactant(s) are combined by blending them together to yield a biocompatible, durable hydrophilic composition. In some cases the surfactant may be dissolved in or along with a surfactant carrier. The surfactant carrier and/or surfactant may be a plasticizer for the thermoplastic aliphatic polyester. Such plasticized aliphatic polyester compositions generally have a lower melt processing temperature, can yield a more flexible output material, and may have a lower glass transition temperature.

Such compositions can be processed to produce hydrophilic layers and fibers suitable for creating woven and non-woven hydrophilic layers. In some embodiments, the composition is melt-processable, such that the composition is capable of being extruded. In some embodiments, the composition is solvent soluble or dispersible and the composition may be solvent cast or solvent spun to form films, fibers, or foams. The melt processable composition of aliphatic polyesters and surfactants exhibit durable hydrophilicity, as do films, fibers, and webs produced from such compositions.

The aliphatic polyester component of the composition of this disclosure typically comprises at least 70 weight percent, in some embodiments, at least 85 weight percent, and even at least 95 weight percent, based on the total weight of the aliphatic polyesters and the surfactants.

As used herein the term "surfactant" means an amphiphile (a molecule possessing both polar and nonpolar regions which are covalently bound) capable of reducing the surface tension of water and/or the interfacial tension between water and an immiscible liquid. The term is meant to include soaps, detergents, emulsifiers, surface active agents, and the like. In applications in which biodegradability is important, it may be desirable to incorporate biodegradable surfactants, which typically include ester and/or amide groups that may be hydrolytically or enzymatically cleaved. In certain embodiments, the surfactants useful in the compositions of the present invention are anionic surfactants selected from the group consisting of alkyl, alkenyl, alkaryl and arakyl sulfonates, sulfates, phosphonates, phosphates and mixtures thereof. Included in these classes are alkylalkoxylated carboxylates, alkyl alkoxylated sulfates, alkylalkoxylated sulfonates, and alkyl alkoxylated phosphates, and mixtures thereof. Aralkyl and alkaryl sulfonates, sulfates, phosphonates and phosphates also may be useful such as branched or straight chain dodecylbenzene sulfonate, sodium salt. In some embodiments, the alkoxylate is made using ethylene oxide and/or propylene oxide with 0-100 moles of ethylene and propylene oxide per mole of hydrophobe. In certain embodiments, the surfactants are selected from the group consisting of sulfonates, sulfates, phosphates, carboxylates and mixtures thereof. In some embodiments, the surfactant is selected from (C8-C22) alkyl sulfate salts (e.g., sodium salt), di(C8-C13 alkyl)sulfosuccinate salts, C8-C22 alkyl sarconsinate, C8-C22 alkyltaurates, C8-C22 alkyl lactylates and combinations thereof.

Certain nonionic polyethoxylated surfactants are useful in improving the absorption rate and/or absorption capacity. In some embodiments, surfactant systems comprising a combination of an anionic surfactant and a polyalkoxylated nonionic surfactant may be used. Generally, the polyalkoxylated nonionic surfactant has at least 50% mole % oxyethylene groups, and more preferably at least 75 mole % oxyethylene groups as a percentage of the polyalkoxylate group. Preferably the nonionic surfactant is a liquid at room temperature which is believed to facilitate migration to the surface. Preferred nonionic surfactants have a branched alkyl chain, an unsaturated alkyl chain, multiple polalkoxylate groups or a combination thereof. Examples include alkyl ether polyalkoxylates (e.g. Tergitol 15-S-7, an ethoxylated secondary alcohol available from Dow Chemical Company, Midland Mich.), alkyl ester polyalkoxylates (e.g. PEG 400 monolaurate, PEG 600 distearate), alkyl amide polyalkoxylates (e.g. PEG 5 lauramide, PEG 6 lauric diethanolamide), alkoxylated sorbitan fatty esters (e.g. PEG 20 sorbitan monolaurate, PEG 40 sorbitan dioleate, etc), alkoxylated esters and ethers of polyhydric alcohols, and the like as well as combinations thereof.

If used, the one or more surfactants may be incorporated at a level suitable to produce the desired result. In some embodiments, surfactant(s) are blended with aliphatic polyester(s) and are present in a total amount of at least 0.5 wt. %, at least 0.75 wt. %, at least 1 wt. %, or at least 2 wt %, based on the total weight of the blended composition. In certain embodiments, in which a very hydrophilic web is desired, or a web that can withstand multiple assaults with aqueous fluid, the surfactant component comprises greater than 2 wt. %, greater than 3 wt. %, or even greater than 5 wt. % of the blended composition. However, in some embodiments, the surfactant(s) are present in a total amount of no greater than 15 wt. %, no greater than 10 wt. %, no greater than 5 wt. %, or even no greater than 3 wt. %, based on the total weight of the aliphatic polyester web.

In some embodiments the webs are formed from multi-component fibers such as bicomponent fibers. In some embodiments it may be desirable to use a sheath/core or side by side fiber construction where the core or one side is essentially free of surfactant or has reduced surfactant in order to improve the strength of the fiber and web. In a particularly preferred embodiment the fibers are spunbond fibers formed using a bicomponent sheath/core die where the core is free of surfactant and the sheath has sufficient surfactant to ensure the web is hydrophilic and absorbent. Generally such constructions have at least 2 wt. % of the sheath comprised of one or more surfactants. More preferably these bicomponent fibers have at least 2.5 wt. % of the sheath comprised of one or more surfactants.

In some embodiments, it may be convenient to use a surfactant predissolved in a nonvolatile carrier. The carrier is typically thermally stable and can resist chemical breakdown at processing temperatures which may be as high as 150° C., 180° C., 200° C. or even 250° C. In some embodiments, the carrier is a liquid at 23° C. Exemplary carriers include polyalkylene glycols such as polyethylene glycol, polypropylene glycol, random and block copolymers of ethylene oxide and propylene oxide, thermally stable polyhydric alcohols such as propylene glycol, glycerin, polyglycerin, and the like. Carriers also may include low molecular weight esters of polyhydric alcohols such as triacetin, glyceryl caprylate/caprate, acetyltributylcitrate, and the like. We have found that these carriers improve absorbent capacity and absorbent rate most likely due to enhancing migration of the surfactant(s) to the surface. In some embodiments the nonvolatile carrier is a pourable liquid at 23° C. In certain embodiments, one or more of the surfactants may be a liquid at 23° C. and may function as both a surfactant and a carrier for other surfactants that are solids or pastes at 23° C.

Since the carrier is substantially nonvolatile it will in large part remain in the composition and may function as an organic plasticizer. As used herein a plasticizer is a compound having a molecular weight less than 10,000 daltons which when added to the polymer composition results in a decrease in the glass transition temperature.

In some embodiments, the absorbent layer comprises a plurality of continuous fibers comprising one or more thermoplastic aliphatic polyesters and a thermoplastic antishrinkage additive in an amount greater than 0 wt. % and no more than 15 wt. % of the fibers. In some embodiments, the fibers exhibit molecular orientation. In some embodiments, the absorbent layer has at least one dimension which decreases by no greater than 10% in the plane of the layer when the layer is heated to a temperature above a glass transition temperature of the fibers, but below the melting point of the fibers. In some exemplary embodiments, the molecular orientation of the fibers results in a bi-refringence value of at least 0.01. In most embodiments, the fibers are microfibers, and particularly fine fibers.

In some embodiments, the aliphatic polyester is semicrystalline. In some embodiments, the thermoplastic antishrinkage additive comprises at least one thermoplastic semicrystalline polymer. In some embodiments, the thermoplastic semicrystalline polymer selected from the group consisting of polyethylene, linear low density polyethylene, polypropylene, polyoxymethylene, poly(vinylidine fluoride), poly(methyl pentene), poly(ethylene-chlorotrifluoroethylene), poly(vinyl fluoride), poly(ethylene oxide), poly(ethylene terephthalate), poly(butylene terephthalate), semicrystalline aliphatic polyesters including polycaprolactone, aliphatic polyamides such as nylon 6 and nylon 66, and thermotropic liquid crystal polymers.

It was found that surface treatment and subsequent drying of fabrics made from polymers having a glass transition temperature, Tg, less than the drying temperature resulted in a significant increase in stiffness, resulting in reduced softness and drapeability. In contrast, adding the surfactant to the polymer composition, e.g., as a melt additive preserves softness and drapeability, and may reduce costs. Also, the addition of surfactants and particularly surfactants in carriers to the melt-processable compositions can reduce the tensile strength of the resulting material significantly. This is believed to be due at least in part to a plasticization of the polymer with resulting decrease in crystallinity. Thus, the present inventors discovered that it may be preferred to add the surfactant to the sheath of a sheath/core bicomponent fiber. Keeping the core free of surfactant and carrier can greatly improve the overall strength. Such an approach may also accelerate migration of the surfactant to the surface of the fiber. Generally, the core represents at least 40% by volume (determined by relative cross-sectional area) of the bicomponent fibers. In some embodiments, the fiber core is at least 50% by volume, e.g., at least 60% by volume and even at least 80% by volume of the bicomponent fibers. A similar effect may be achieved using a side by side fiber configuration where one side comprises the surfactant composition and the other does not. In some embodiments, the surfactant free side (or reduced surfactant) is at least 50% by volume, e.g., at least 60% by volume and even at least 80% by volume of the bicomponent fibers.

In some embodiments, the absorbent layer will exhibit a basis weight, which may be varied depending upon the particular end use of the web. Typically, the absorbent layer has a basis weight of no greater than about 1000 grams per square meter (gsm). In some embodiments, the absorbent layer has a basis weight of from about 1.0 gsm to about 500 gsm. In other embodiments, the absorbent layer has a basis weight of from about 10 gsm to about 300 gsm. For use in some applications such as medical fabrics, including surgical drapes, surgical gowns and sterilization wraps, the basis weight is typically from about 10 gsm to about 100 gsm, e.g., 15 gsm to about 60 gsm.

As with the basis weight, the absorbent layer will exhibit a thickness, which may be varied depending upon the particular end use of the web. Typically, absorbent layer has a thickness of no greater than about 300 millimeters (mm) In some embodiments, the absorbent layer has a thickness of from about 0.5 mm to about 150 mm when measured with essentially no pressure applied such as by using an optical comparator. In other embodiments, the absorbent layer has a thickness of from about 1.0 mm to about 50 mm. For use in some applications such as medical fabrics, including surgical drapes, surgical gowns and sterilization wraps, the thickness is generally from about 0.1 mm to about 10 mm, e.g., 0.25 mm to about 2.5 mm.

In certain embodiments, the absorbent layer comprises at least one nonwoven fibrous web, which can be prepared by fiber-forming processes in which filaments of fiber-forming material are formed by extrusion of a mixture of one or more thermoplastic aliphatic polyesters with a surfactant additive composition in an amount greater than 0.25% and no more than 10% by weight of the mixture to which it is added (i.e. sheath, core, entire fiber etc.), subjected to orienting forces, and passed through a turbulent field of gaseous currents while at least some of the extruded filaments are in a softened condition and reach their freezing temperature (e.g., the temperature at which the fiber-forming material of the filaments solidifies) while in the turbulent field. The surfactant composition may comprise one or more of the previously mentioned surfactants and optionally a surfactant carrier. Such fiber forming processes include, for example, melt-spinning (i.e. spunbond), filament extrusion, electro-spinning, gas jet fibrillation or combinations thereof.

In some embodiments, absorbent nonwoven fibrous webs can be prepared by fiber-forming processes in which substantially non-molecularly oriented filaments of fiber-forming material are formed from a mixture of one or more thermoplastic aliphatic polyesters with a surfactant additive in an amount greater than 0.25% and no more than 10% by weight of the mixture to which it is added, before or during extrusion. In some exemplary embodiments, the fibers may be formed using a melt-blowing (e.g. BMF) process. In some exemplary embodiments, the fibers may be formed using a spunbond process.

The multilayer articles of the present disclosure also include a barrier layer. The barrier layer may comprise one or more plies. As used herein the term "barrier layer" refers to a layer that does not allow liquid water to pass through at a pressure of 5 kPa when tested by the Hydrohead method as described in I. S. EN 20811-1993 Textiles—Determination of Resistance to Water Penetration-Hydrostatic Pressure Test. In some embodiments, barrier layers exceed 7.5 kPa or even 10 kPa when tested by this method. In some embodiments, barrier layers do not allow liquid water to pass through when tested by the Hydrohead method as described in I. S. EN 20811-1993 at 6 kPa per minute pressure increase with the barrier side up and no other support.

In some embodiments, suitable barriers include nonporous films. Generally, the barrier layers are polyolefin barrier layers. As used herein, a "polyolefin barrier layer" is a barrier layer wherein at least 60 wt. % of polymers or copolymers present in the barrier layer comprise at least 50 wt. % olefin monomer units. In some embodiments, at least 70 wt. % or even at least 80 wt. % polymers or copolymers in the polyolefin barrier layer comprise at least 50 wt. % olefin monomer units. In some embodiments, the polymers and copolymers comprise at least 70 wt. %, e.g., at least 80 wt. %, or even at least 90 wt. % olefin monomer units. In some embodiments, at least one polymer or copolymer consists of olefin monomers. In some embodiments, at least 80 wt. %, in some embodiments, at least 90 wt. %, or even at least 95 wt. % of the polymers or copolymers present in the barrier layer consist of olefin monomers. Exemplary materials suitable for use in the barrier layer include polyolefins such as low density polyethylene (LDPE), linear low density polyethylene (LLDPE), metallocene polyethylene, polypropylene (PP), metallocene polypropylene, and the like. Suitable polymers for the barrier layer also include blends of polyethylenes, blends of polypropylenes, blends of polyethylene and polypropylene, blend polyethylene and/or polypropylene with suitable amorphous polymers, copolymers made from ethylene and propylene monomers, and blends of such copolymers with polyethylenes, polypropylenes, suitable amorphous polymers, semi-crystalline/amorphous polymers, heterophasic polymers, or combinations thereof. Other useful polymers that may be used in the barrier layer include elastomeric thermoplastic polymers. Examples of useful polymers that can be included in the barrier layer include those available under the trade names EXXPOL, EXCEED, and EXACT from Exxon Chemical Company of Baytown, Tex.; those available under the trade names ENGAGE, ACHIEVE, ATTAIN, AFFINITY, and ELITE from Dow Chemical Company of Midland, Mich.

In some embodiments, the absorbent layer may be bonded directly to the barrier layer. Despite the individual advantages of using a hydrophilic, surfactant-treated aliphatic polyester absorbent layer and a polyolefin barrier layer, the present inventors found that bonding these layers to each other to form the desired finished multilayer article was difficult. It was particularly difficult to bond these incompatible layers to each other to produce an article that could withstand use in a humid, moist, or wet environment. For example, while sterilization in high humidity increases absorbency it can greatly decrease the adhesion of the barrier film to the nonwoven when tested by a hydrohead method. In addition, the present inventors discovered that, contrary to conventional wisdom, corona treatment of the absorbent layer decreased the hydrohead adhesion values.

Absorbent layers are generally polar and hydrophilic, while barrier layers are typically nonpolar and hydrophobic. As a result, hydrophilic absorbent layers are generally incompatible with and bond poorly to common barrier layers, particularly polyolefin-based film barriers.

The present inventors have surprisingly discovered a variety of approaches to overcome one or more of these and other difficulties, while delivering one or more of the desired advances in drapes. In one approach, a tie layer having a high content of polar monomer is used to bond the absorbent layer to the barrier layer. In another approach, a multiply absorbent layer is used with one ply having little or no surfactant and a second ply containing sufficient surfactant to make the absorbent layer immediately and rapidly absorbent. The low-surfactant content first ply is positioned between and bonds together the barrier layer and the high-surfactant content second layer. In some embodiments, combinations of these methods may be used.

Figure 1:
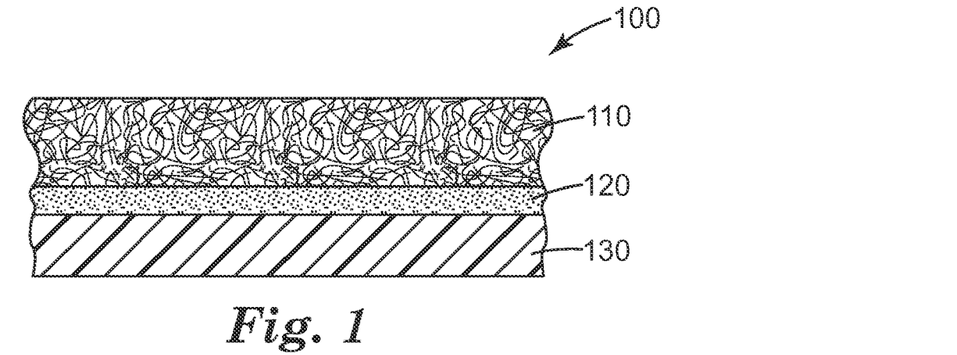
FIG. 1 illustrates an exemplary multilayer article according to some embodiments of the present disclosure.

Referring to FIG. 1, in some embodiments, absorbent layer 110 of multilayer article 100 is indirectly bonded to barrier layer 130 using tie-layer 120. Although shown as a single layer, in some embodiments, two-or more intermediate layers may be used. In one aspect of this disclosure, the present inventors have discovered certain tie-layers suitable for bonding absorbent layers to barrier layers. For example, the present inventors have discovered that a tie layer having high polar monomer content and, optionally, a reactive group capable of covalently reacting with a hydroxyl group can improve the bond between incompatible absorbent and barrier layers.

In some embodiments, the tie layer comprises a copolymer of polyolefin monomer(s) with a polar monomer. Exemplary polar monomers include vinyl acetate (VA); C1-C8 acrylates such as ethyl acrylate (EA), methyl acrylate (MA), butyl acrylate (BA), and 2-ethylhexyl acrylate; and C1-C4 acrylic acids (e.g., acrylic acid and methacrylic acid). In some embodiments, the copolymer of the tie layer comprises a high content of the polar monomer(s). For example, when the tie layer comprises an ethylene vinyl acetate copolymer (EVA), the vinyl acetate content may be greater than 30%, 35%, and even greater than 40% by weight of the copolymer. Other exemplary tie layer include copolymers of ethylene and C1-C8 acrylates such as ethylene ethyl acrylate (EEA), ethylene methyl acrylate (EMA), ethylene butyl acrylate (EBA), and 2 ethylhexyl acrylate. In some embodiments, the copolymers have relatively high acrylate content by weight. In some embodiments, the acrylate is present at greater than 15%, 17%, and preferably 20% by weight in the copolymer. In some embodiments, the copolymers have relatively high acrylic acid content, e.g., copolymers of ethylene and C1-C4 acrylic acids (e.g., EAA). In some embodiments, the acrylic acid content is greater than 7 wt. %, or even greater than 9 wt. % acrylic acid. Exemplary copolymers include EVA copolymers available from LANXESS GMBH under the trade name LAVAMELT, e.g., LAVAMELT 450, and methyl acrylate ethylene copolymers (EMA) such as those available under the trade name ELVALOY from Dupont, such as ELVALOY AC 12024.

In some embodiments, the tie layer also comprises one or more polymers comprising a reactive group. In some embodiments, the reactive group is capable of covalently bonding to a hydroxyl group such as the terminal groups on an aliphatic polyester. Examples of such polymers include those comprising anhydride groups or epoxy groups. In some embodiments, the tie layer is a copolymer comprising at least three different monomers: an olefin monomer (e.g., ethylene), a polar nonreactive monomer (e.g., vinyl acetate or a methacrylate monomer) and a reactive monomer (e.g., a monomer having an anhydride or epoxy group). In some embodiments, the copolymer of the tie layer comprises greater than 0.5, e.g., greater 1, greater than 3, or even greater than 5 wt. % reactive monomer and greater than 10, greater than 15, or even greater than 18 wt. % nonreactive polar monomer. Exemplary reactive tie layer copolymers include those available under the trade name TYMAX from Westlake Chemical Corp., Houston Tex. (e.g., TYMAX GA7001 which is believed to be a terpolymer of 20% methyl acrylate, ethylene, and an anhydride containing reactive monomer) and those available under the trade name LOTA-DUR from Arkema (e.g., LOTADUR AX8900 which is believed to be a terpolymer of 24% methylacrylate, 8% glycidylmethyacrylate and 68% ethylene.

In some embodiments, the tie layer may include one or more plasticizers. Exemplary plasticizers include alkyl benzoates such as those available under the trade name FIN-SOLVE from Innospec Performance Chemicals.

In some embodiments, the tie layer itself can serve as the barrier layer. For example, in some embodiments, the multilayer article comprises a surfactant-treated, hydrophilic, absorbent layer with a barrier layer directly bonded to the absorbent layer. In some embodiments, the barrier layer is selected from those materials identified herein as suitable for use as a tie layer.

In some embodiments, one or both of the tie layer and the barrier layer comprise a tackifier. A wide variety of resinous (or synthetic) materials commonly used in the art to impart or enhance adhesion of the tie layer to the aliphatic polyester nonwoven and/or to the polyolefin film core layer may be used as a tackifier. In some embodiments, the tackifiers have a ring and ball softening point greater than 90° C. and in some embodiments, greater than 100° C. according to ASTM E 28 and a weight average molecular weight of greater than 700 and in some embodiments, greater than 800 or even greater than 900 g/mol.

Exemplary tackifiers include rosin, rosin esters of glycerol or pentaerythritol, hydrogenated rosins, polyterpene resins such as polymerized beta-pinene, coumaroneindene resins, "C5" and "C9" polymerized petroleum fractions, and the like. Suitable commercially available tackifiers include synthetic ester resins, such as that available under the trade name FORAL (e.g., FORAL 85) from Hercules Inc., Wilmington, Del., and aliphatic/aromatic hydrocarbon resins, such as those available under the trade name ESCOREZ (e.g., ESCOREZ 5690) from Exxon Chemical Co., Houston, Tex. and REGALREZ (e.g., REGALREZ 6108 and 3102) from Eastman Chemical Company Kingsport, Tenn.

Generally, the tackifier is added in amounts required to achieve the desired tack, adhesion, and/or coefficient of friction level. This is typically achieved by adding from 1 part to about 100 parts by weight of tackifier per 100 parts by weight of the tie layer copolymer. In some embodiments, the tackifier is added at from 2 to 20 parts by weight tackifier to 100 parts by weight of the tie layer copolymer. The tackifier is selected to provide the tie layer copolymers with an adequate degree of tack while molten to promote adhesion and to maintain their adhesion when cooled. As is known in the art, not all tackifier resins interact with the tie layer copolymer in the same manner; therefore, some minor amount of experimentation may be required to select the appropriate tackifier resin and concentration to achieve the desired adhesive performance. Such minor experimentation is well within the capability of one skilled in the adhesive art.

The present inventors also observed that surfactant in the surfactant-treated layer can migrate to other layers and to the external major surfaces of the multilayer article. This migration was accelerated by winding the material up on itself to form a jumbo and again when the product was folded upon itself. It was also discovered that this migration was greatly accelerated by moisture. Thus, in some embodiments, the multilayer articles are treated with moisture or high humidity. For example, they may be exposed to steam in line. In some embodiments, the articles are sterilized using a method that incorporates high humidity, e.g. greater than 50% RH, in some embodiments, greater than 65% RH, greater than 80% RH and even greater than 90% RH. For example, in some embodiments, the articles are sterilized using ethylene oxide gas in a humidified chamber. This has been shown to greatly enhance the absorbency of the sterilized article.

As an alternative to, or in addition to the use of a tie layer, the present inventors have also discovered that advantages can be achieved using a multi-ply (e.g., a dual-ply) absorbent layer wherein the outermost ply contains sufficient surfactant to achieve rapid absorbency and the innermost ply, which is bonded to the barrier layer, contains little to no surfactant. For example, surprisingly, the present inventors discovered that by providing at least one inner ply between the surfactant treated outer ply of the absorbent layer and the barrier layer can greatly improve adhesion.

Figure 2:
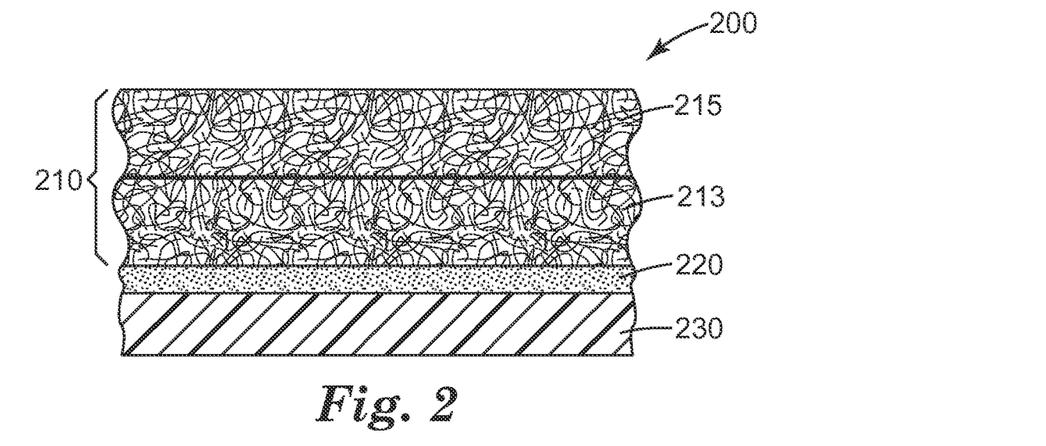
FIG. 2 illustrates another exemplary multilayer article according to some embodiments of the present disclosure.

Referring to FIG. 2, multilayer article 200 includes absorbent layer 210 and barrier layer 230. Absorbent layer 210 includes at least two plies. First ply 213 comprises substantially less surfactant than second ply 215. In some embodiments, the first ply is directly bonded to the barrier layer. In some embodiments, first ply 213 is indirectly bonded for barrier layer 230 using, e.g., tie layer 220.

In some embodiments, the first ply comprises at least 50 wt. % less surfactant, e.g., at least 75 wt. % less surfactant than the second ply. In some embodiments, the first ply comprises at least 90 wt. %, at least 95 wt. %, or even at least 99 wt. % less surfactant than the second ply. In some embodiments, the first ply is substantially surfactant-free, i.e., the first ply comprises no greater than 0.2 wt. %, in some embodiments, no greater than 0.1 wt. %, no greater than 0.01 wt. %, or even no greater than 0.005 wt. % surfactant based on the total weight of the first ply.

Such a multi-ply absorbent layer may be produced, for example, on a multiple beam spunbond or melt blown machine where one beam has surfactant added and the other beam does not. Surprisingly, the surfactant does not prevent the aliphatic polyester fibers from thermally bonding together with themselves in the high-surfactant content ply or with the non-surfactant treated fibers of the low-surfactant content ply. Thus, the layered nonwoven is preferably thermally point bonded. For example, a heated calendar roll having the desired pattern may be used. In order to preserve softness and flexibility/hand/drapeability, the bond pattern is preferably discontinuous and represents less than 30% of the projected area of the major surface. In some embodiments, the bond pattern is less than 20% of the projected area.

In some embodiments, a multi-ply absorbent layer may be formed by overlaying on a support layer an absorbent nonwoven fibrous web comprising an overlayer of microfibers on an underlayer comprising a population of sub-micrometer fibers, such that at least a portion of the sub-micrometer fibers contact the support layer. In such embodiments of a multi-ply absorbent layer, it will be understood that the term "overlayer" is intended to describe an embodiment wherein at least one ply overlays another ply in a multi-ply composite web. Furthermore, reference to "a ply" is intended to mean at least one ply, and therefore each illustrated embodiment of a multi-ply layer may include one or more additional plies within the scope of the disclosure.

Figure 3:
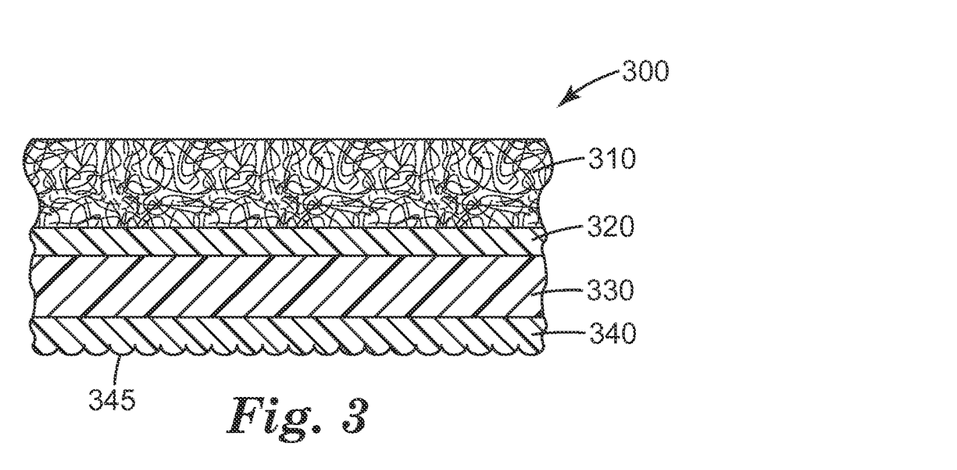
FIG. 3 illustrates yet another exemplary multilayer article according to some embodiments of the present disclosure.

In some embodiments, additional layers may be included. For example, in some embodiments, the exposed surface of the barrier layer (i.e., the surface opposite the tie layer) may be covered by an additional layer or coating. For example, in some embodiments, the texture or feel of the barrier layer may be modified. In some embodiments, the coefficient of friction of the surface may be altered, e.g., increased. Referring to FIG. 3, another multilayer article according to some embodiments of the disclosure is illustrated. Multi-layer article 300 includes absorbent layer 310, which may include be a single-, or multi-ply layer. Tie-layer 320 is used to indirectly bond absorbent layer 310 to barrier layer 330. Surface layer 340 is disposed on the barrier layer, opposite the tie layer. In some embodiments, exposed surface 345 of surface layer 340 may be textured to, e.g., adjust feel and/or coefficient of friction.

Generally, any of a wide variety of materials may be used to form the surface layer. In some embodiments, the surface layer may have the same composition as the tie layer. In some embodiments, the surface layer may be coextruded with the barrier and/or tie layer. In some embodiments, the surface layer may be applied, e.g., coated or extruded, in a subsequent step.

In some embodiments, additional layers may be included. For example, in some embodiments, a multilayer barrier film may be used. In some embodiments, multiple surface layers may be applied.

Other optional components may be included in one or more layers of the articles described herein. For example, in some embodiments, an antimicrobial component may be added to impart antimicrobial activity to the compositions. The antimicrobial component is that component of the composition that provides at least part of the antimicrobial activity, i.e., it has at least some antimicrobial activity for at least one microorganism. It is preferably present in a large enough quantity to be leached from the composition and kill bacteria. It may also be biodegradable and/or made or derived from renewable resources such as plants or plant products. Biodegradable antimicrobial components can include at least one functional linkage such as an ester or amide linkage that can be hydrolytically or enzymatically degraded.

Examples of antimicrobial components suitable for use in the present invention include those described in Applicants' co-pending application, U.S. Patent Application Publication No. US2008/0142013, and incorporated by reference herein in its entirety. Certain antimicrobial components are uncharged and have an alkyl or alkenyl hydrocarbon chain containing at least 7 carbon atoms. For melt processing, preferred antimicrobial components have low volatility and do not decompose under process conditions. The preferred antimicrobial components contain less than 2 wt. % water, and more preferably less than 0.10 wt. % (determined by Karl Fischer analysis). Moisture content is kept low in order to prevent hydrolysis of the aliphatic polyester and to give clarity to extruded film. Certain antimicrobial components are amphiphiles and may be surface active. For example, certain antimicrobial alkyl monoglycerides are surface active. Certain cationic antimicrobial amine compounds also may be useful as described in US patent application 20080142023. For certain embodiments of the invention that include antimicrobial components, the antimicrobial component is considered distinct from a surfactant component.

When used, the antimicrobial component content (as it is ready to use) is typically at least 1 wt. %, 2 wt. %, 5 wt. %, 10 wt. % and sometimes greater than 15 wt. %. In certain embodiments, in which a low strength is desired, the antimicrobial component comprises greater than 20 wt. %, greater than 25 wt. %, or even greater than 30 wt. % of the composition.

In some embodiments, one or more of the layers may further comprise organic and inorganic fillers. In some embodiments, biodegradable, resorbable, or bioerodible inorganic fillers may be particularly appealing. These materials may help to control the degradation rate of the polymer composition. For example, many calcium salts and phosphate salts may be suitable. Exemplary biocompatible resorbable fillers include calcium carbonate, calcium sulfate, calcium phosphate, calcium sodium phosphates, calcium potassium phosphates, tetracalcium phosphate, .alpha.-tricalcium phosphate, beta-tricalcium phosphate, calcium phosphate apatite, octacalcium phosphate, dicalcium phosphate, calcium carbonate, calcium oxide, calcium hydroxide, calcium sulfate dihydrate, calcium sulfate hemihydrate, calcium fluoride, calcium citrate, magnesium oxide, and magnesium hydroxide. A particularly suitable filler is tribasic calcium phosphate (hydroxy apatite).

In some embodiments, plasticizers may be used with the aliphatic polyester thermoplastic and include, for example, glycols such glycerin; propylene glycol, polyethoxylated phenols, mono or polysubstituted polyethylene glycols, higher alkyl substituted N-alkyl pyrrolidones, sulfonamides, triglycerides, citrate esters, esters of tartaric acid, benzoate esters, polyethylene glycols and ethylene oxide propylene oxide random and block copolymers having a molecular weight less than 10,000 daltons preferably less than about 5000 daltons, more preferably less than about 2500 daltons; and combinations thereof.

Other additional components include antioxidant, colorant such as dyes and/or pigments, antistatic agents, fluorescent brightening agents, odor control agents, perfumes and fragrances, active ingredients to promote wound healing or other dermatological activity, combinations thereof and the like.

Exemplary multilayer articles according to some embodiments of the present disclosure were prepared using the materials summarized in Table 1.

TABLE 1

Summary of materials used in the examples.

| I.D. | Description | Source (Trade name) |
| --- | --- | --- |
| PLA-1 | Polylactic acid | Natureworks LLC, Blair, Nebraska (INGEO 6202D) |
| PLA-2 | Polylactic acid | Natureworks LLC, Blair, Nebraska (INGEO 6751D) |
| DOSS | 50% Docusate Sodium in Polyethylene Glycol 400 | JLK Industries, Coopersburg, Pennsylvania (JDOSS 50P) |
| PP | Polypropylene | Total Petrochemical, Brussels, Belgium (TOTAL 3868) |
| LDPE | Low density polyethylene | Chevron Phillips Chemical Company LP, The Woodlands, Texas (MARFLEX 1019) |
| LLDPE | Linear low density polyethylene | DOW Chemical Company (DOWLEX 2517) |
|  | PEG-5 Cocamide | Global 7 Industries, Franklin New Jersey (HETOXAMIDE C4) |
| Tack-1 | 100% hydrogenated C9 aromatic resin | Eastman Chemical, Kingsport, Tennessee (REGALREZ 6108) |
| Tack-2 | 30% hydrogenated C9 aromatic resin | Eastman Chemical (REGALREZ 3102) |
| Tack-3 | 50% hydrogenated C9 aromatic resin | Eastman Chemical (REGALITE S5100) |
| Tack-4 | 50% hydrogenated C9 aromatic resin | Eastman Chemical (REGALITE S5090) |
| Tack-5 | 70% hydrogenated C9 aromatic resin | Eastman Chemical (REGALITE S7125) |
|  | C12-C15 alkyl benzoate | Innospec Active Chemicals (FINSOLV TN) |
| EMA | Ethylene-methyl acrylate copolymer | Dupont, Wilmington, Delaware (ELVALOY AC 12024S) |
| EAA | Ethylene-acrylic acid copolymer with 9.7% acrylic acid | DOW Chemical Company (PRIMACORE 3460) |
| RxGMA-1 | HDPE with greater than 1.0 wt. % grafted maleic anhydride | DOW Chemical Company Performance Plastics (AMPLIFY GR 204) |
| RxGMA-2 | LDPE with greater than 0.5 wt. % grafted maleic anhydride | DOW Chemical Company Performance Plastics (AMPLIFY GR 209) |
| RxGMA-3 | Plastomer with greater than 0.5 wt. % grafted maleic anhydride | DOW Chemical Company Performance Plastics (AMPLIFY GR 216) |
| RxCMA-1 | Ethylene-maleic anhydride copolymer (Mw = 60,000) | Vertellus Health and Specialty Products, LLC (ZeMac E60) |
| RxCMA-2 | Ethylene-maleic anhydride copolymer (Mw = 400,000) | Vertellus Health and Specialty Products, LLC (ZeMac E400) |
| RxAH-1 | Anyhydride modified ethylene-methyl acrylate copolymer | Westlake Chemical Corporation, Houston Texas (TyMax GA7001) |
| RxAH-2 | Anyhydride modified ethylene-methyl acrylate copolymer | Westlake Chemical Corporation (TyMax GA7501) |
| EVA-20 | Ethylene vinyl acetate (EVA) copolymer with 20% vinyl acetate (VA) content | DuPont Company, Willmington, Delaware (ELVAX 3178Z) |
| EVA-25 | EVA with 25 wt. % VA content | DuPont Company (ELVAX 350) |
| EVA-28a | EVA with 28 wt. % VA content | DuPont Company (ELVAX 3180) |
| EVA-28b | EVA with 28 wt. % VA content | Celenase; Edmonton, AB (ATEVA 2821A) |
| EVA-33 | EVA with 33 wt. % VA content | Arkema Technical Polymers Division, Colombes Cedex, France (EVATANE 33-15) |
| EVA-45 | EVA with 45% wt VA content | Lanxess Corporation; Pittsburgh, PA (LEVAMELT 456) |
| MA-EVA1 | Maleic anhydride-modified EVA copolymer | Dupont Company (FUSABOND C190) |
| MA-EVA2 | Maleic anhydride-modified EVA copolymer | Dupont Company (BYNEL E418) |
|  | PMMA-PBA-PMMA copolymer | Kuraray America (KURARITY LA2250) |
| Blue MB1 | 30 pbw blue pigment in 70 pbw PLA | Master batch prepared by 3M |
| Blue MB2 | Blue pigment in low density polyethylene | Techmer Polymer Modifiers, Clinton, Tennessee |
| Blue MB3 | Blue pigment in polypropylene | Techmer Polymer Modifiers |

Example EX-1 was a multilayer article formed using a PLA-based, hydrophilic nonwoven absorbent layer. A three-layer structure comprising a tie-layer, a barrier layer, and an optional outer layer was extrusion coated using a co-extrusion cast film process.

The nonwoven absorbent layer was a single layer made using one spunbond beam. The nonwoven was produced using PLA that was treated to increase hydrophilicity by incorporating a melt additive surfactant package. The resulting composition of the hydrophilic, nonwoven, absorbent layer was 1.5% by weight PEG-5 Cocamide, 1.5% by weight DOSS (50% solution); 2% by weight PP; and 93% to 94% by weight PLA-1. The composition also included 1 to 2% by weight Blue MB1.

The multilayer structure was applied to the nonwoven, absorbent layer using a CLOEREN feedblock, with a B-A-C configured selector plug, and a drop die, resulting in a three-layer construction. For consistency, as used herein, the "A" layer refers to the barrier; the "B" layer refers to the tie layer, and the "C" layer refers to any optional surface layers. Each layer was fed to the common feedblock using a separate single screw extruder. As the melt exited the die lip, it was laid on the nonwoven as it entered the nip point of a rubber back roll and metal, matte finish, cast roll. The multilayer structure was applied such that the tie layer (the B layer) was adjacent to the nonwoven, absorbent layer, and the C layer was adjacent the cast roll such that it took on the matte finish.

As summarized in Table 2, both the tie layer and the outer layer of the three-layer structure (Layers B and C) consisted of EMA (24% methyl acrylate content; melt flow index ("MFI") of 20 g/10 min at 190° C.). Barrier layer (Layer A) consisted of a blend of 37 parts by weight LDPE (MFI of 16 g/10 min at 190° C., 2.16 kg), 50 parts LLDPE (MFI of 25 g/10 min at 190° C., 2.16 kg), and 13 parts of Blue MB2. These compositions were coated with a layer to layer ratio of 1:2:1 (B:A:C).

Examples EX-2 and EX-3 were prepared in the same manner except a tackifier was included in Layers A and C, as summarized in Table 2. The EMA and hydrocarbon resin were pre-compounded at a weight ratio of 90:10 using a twin screw extruder and pelletizer to form a master batch. This master batch was then blended 50:50 by weight with additional EMA. These compositions were coated with a layer to layer ratio of 2:2:0.1 (B:A:C).

In Examples EX-1 through EX-3, the processing temperature of the B-layer was approximately 243° C. and the processing temperature of the A-layer was about 336° C. The C-Layer for Examples EX-1 and EX-3 were processed at 236-245° C., while the C-Layer was processed at about 257° C. for Example EX-2.

Adhesion of the barrier layer to the nonwoven layer was measured according to the procedure specified in the EN Standard for Textiles—Determination of Resistance to Water Penetration—Hydrostatic Pressure Test (EN 20811, 1993), hereinafter referred to as the "Hydrohead Test." Samples were tested using a pressure increase rate of 6 kPa per minute with the barrier film side up and no other support.

The tests were performed shortly after coating, and the results are reported in Table 2. Failure occurred at the nonwoven, absorbent layer/tie layer interface. Significant bloating of the sample occurred as the pressure increased and ultimately resulted in delamination. The pressure at which an initial small bubble of film delaminated was recorded as the initial value. The pressure at which greater than 70% delamination had occurred was recorded as the failure value.

TABLE 2

Results for Examples EX-1 to EX-3.

| Ex. | Tie layer (layer B) | Initial (kPa) | Failure (kPa) |
|---|---|---|---|
| EX-1 | 100% EMA | 3.1 | 4.5 |
| EX-2 | 95% EMA + 5% Tack-1 | 10.2 | 10.3 |
| EX-3 | 95% EMA + 5% Tack-2 | 5.5 | 6.6 |

Most medical fabrics have a need to be sterile. A first set of samples were selected from EX-2 and sterilized using ethylene oxide gas (EtO) in a sterilizer available under the trade name SteriVac 5XL from 3M Company, St. Paul, Minn. The relative humidity was 56% to 63% during ethylene oxide sterilization at a temperature of 50° C. for one hour. The sample was then aerated at 45-50° C. for six hours. A second set of samples from EX-2 was sterilized using gamma radiation at a treatment level of about 45 to 48 kGy. The Hydrohead Test was used to measure the failure values for unsterilized, ethylene oxide sterilized, and gamma radiation sterilized materials, as reported in Table 3.

TABLE 3

Effects of sterilization on delamination of samples of EX-2.

| Sample | Failure (kPa) |
|---|---|
| Unsterilized EX-2 | 21.7 |
| EtO Sterilized EX-2 | 8.6 |
| Gamma Sterilized Ex-2 | 11.9 |

First, comparing the failure pressure of the unsterilized EX-2 sample in Table 3 (21.7 kPa) to the value recorded in Table 2 (10.3 kPa), there was a significant increase in the bond strength upon aging of the sample. The results reported in Table 2 were based on tests conducted shortly after the samples were prepared. The results reported in Table 3 were obtained using samples that had aged for approximately three months.

Second, it appears that sterilization can decrease adhesion. However, even after sterilization, the failure pressure for sample EX-2 (with tackifier) was greater than the failure pressure for unsterilized sample EX-1 (without tackifier).

Samples were prepared using absorbent layers prepared from bicomponent fibers. These absorbent layers were prepared as two-ply structures produced using a two-beam spunbond process. One or both layers were treated with surfactant to increase hydrophilicity.

Example 4 included two plies made of a PLA-based web surfactant-treated to increase the hydrophilicity. Both layers were prepared fibers made up of approximately 68% by volume of a core comprising only PLA-1 with about 0.75 to 1.0 wt. % Blue MB1. The sheath made up about 32% of the fiber volume, and was made of 95 wt. % PLA-1 with 1.5 wt. % PEG-5 Cocamide, 1.5 wt. % DOSS, and 2 wt. % PP.

Example 5 included two plies made of a PLA-based web, but only one ply was surfactant-treated to increase hydrophilicity. The treated, hydrophilic ply was prepared from the core-sheath bicomponent fibers of Example 4. The untreated ply was prepared from fibers containing 1.5 wt. % PP blended with PLA-1.

Example 6 included two plies made of a PLA-based web, but neither ply was surfactant-treated to increase hydrophilicity. The core of the fibers contained 98.9 wt. % PLA-1, 1 wt. % PP, and 0.1 wt. % titanium dioxide. The sheath contained 99 wt. % PLA-1 and 1 wt. % PP.

For each of Examples EX-4 through EX-6, a multi-layer structure was extrusion coated to apply a tie-layer and barrier film to the absorbent layer. The total thickness of the multilayer structure was 23 to 30 microns with an A:B ratio of 3:1. The tie layer (Layer B) contained 95 wt. % EMA and 5 wt. % Tack-1. The barrier film (Layer A) was a blend of 42.5 wt. % LDPE, 42.5 wt. % LLDPE, and 15 wt. % Blue MB2. Examples EX-4 and EX-5 were run with extrusion temperatures of 234-237° C. for both the A and B layers. In Example EX-6, the process temperature was 248° C. for Layer A and 243° C. for Layer B.

Within thirty minutes of extrusion coating, the samples were subjected to the Hydrohead Test. For Example EX-4, the tie-layer was applied to a surfactant-treated ply. For Examples EX-5 and EX-6, the tie layer was applied to the ply of the absorbent layer that was not treated. The results are summarized in Table 4.

Examples EX-4 and EX-5 were sterilized using ethylene oxide gas at a relative humidity of 56 to 63% and a temperature of 51° C. The samples were aerated at 45 to 50° C. for six hours and subjected to the Hydrohead Test. These results are also summarized in Table 4.

The absorbent capacity of Examples EX-4 through EX-6 was also measured according to the following Absorbance Test. A ten centimeter by ten centimeter sample was cut from each example and weighed to obtain a dry weight. The samples were then floated on top of fresh deionized water in an immersion tank, with the non-woven, absorbent layer facing down into the water. No additional force was applied to submerge the sample. After sixty seconds, the sample was lifted from the water with a forceps and held by a corner to drip for five seconds. The sample was then held by an adjacent corner and allowed to drip for an additional five seconds. Care was taken not to shake any water from the sample. The resulting samples were weight to obtain a raw wet weight. Upon removing the sample, water remained on the balance. The weight of this water was recorded and subtracted from the raw wet weight to obtain the true wet weight. Absorbent capacity was calculated as the ratio of the true wet weight minus the dry weight divided by the dry weight. The results are reported as a percent in Table 4.

TABLE 4

Results for multiply absorbent layers.

| I.D. | Failure (kPa) Unsterilized | Sterilized | Absorbent capacity |
|---|---|---|---|
| EX-4 | 10.6 | 6.4 | 256% |
| EX-5 | 20.3 | 14.2 | 222% |
| EX-6 | 15.6 | Not tested | Not tested |

Corona treatment has been commonly used to improve adhesion between layers. Two samples of a two-ply, surfactant-treated absorbent layer were prepared as described in Example EX-4. Both samples were extrusion coated with a two layer composition. The tie layer (Layer B) contained 95 wt. % EMA and 5 wt. % Tack-1. The barrier film consisted of 55 wt. % LDPE, 25 wt. % LLDPE, and 20 wt. % Blue MB2. The process temperature for both the A and B Layers was 238-243 C. Example EX-7 was prepared without corona treatment. The absorbent layer of Example 8 was corona treated at 0.3 Joules per square centimeter just prior to entering the casting station of the extrusion coater. The Hydrohead Test was performed on samples just after extrusion coating, and again after ethylene oxide sterilization. The sterilization was performed at the same conditions as Example EX-2. The results are summarized in Table 5. Contrary to expected results, corona treatment led to a decrease in the adhesion as measured using the Hydrohead Test.

TABLE 5

Results using corona treated absorbent layers.

| I.D. | Corona treated | Final (kPa) Unsterilized | Sterilized |
|---|---|---|---|
| EX-7 | No | 9.7 | 6.9 |
| EX-8 | Yes | 7.7 | 4.2 |

The samples of Example EX-9 were prepared in the same manner as EX-1, unless otherwise noted. The non-woven absorbent layer of EX-9 was prepared from a blend of PLAs and included an alternative surfactant package. The resulting composition of the fibers was 55.3 wt. % PLA-1, 40.0 wt. % PLA-2, 2.6 wt. % DOSS, 1.7 wt. % PP, and 0.43 wt. % Blue MB3.

Potential tie layer compositions were evaluated by extrusion coating only the tie layer onto the absorbent layer. The tie-layer composition was melted and extruded using a 25 mm twin screw extruder. The throughput and pressure were controlled using a melt pump at the end of the extruder. The resulting tie-layer thickness was 18 to 25 microns. The tie layers were processed at 204° C., except for Examples EX-9D and 9E, which had low tackifier concentrations, and were processed at 182° C. The samples were evaluated using the Hydrohead and Absorbance Tests.

TABLE 6

Delamination and Absorbent capacity results for various tie layers.

| EX- | EMA (wt. %) | Tackifier Type | wt. % | Initial (kPa) | Absorbent capacity |
|---|---|---|---|---|---|
| 9A | 100 | none | | 4.6 | 241% |
| 9B | 95 | Tack-3 | 5% | 11.0 | 210% |
| 9C | 90 | Tack-3 | 10% | 12.6 | 221% |
| 9D | 98.75 | Tack-2 | 1.25% | 17.9 | Not tested |
| 9E | 97.5 | Tack-2 | 2.5% | 18.8 | Not tested |
| 9F | 95 | Tack-2 | 5% | 18.5 | 166% |
| 9G | 90 | Tack-2 | 10% | 18.7 | 184% |
| 9H | 95 | Tack-1 | 5% | 13.5 | 212% |
| 9I | 90 | Tack-1 | 10% | 18.4 | 204% |

The preceding examples used a tie layer wherein methyl acrylate was the polar co-monomer. The following examples were prepared using acrylic acid as the polar co-monomer. These examples were evaluated in a multi-layer extrusion coating. The layer configuration was B-A-B at a ratio of 1:2:1. Various tackifiers were blended with EAA, and coated onto a surfactant treated hydrophilic PLA-based spunbond similar to the nonwoven used in previously in Example 9. The results were compared to a sample using 100% EMA as the tie-layer. The barrier layer consisted of 56 wt. % LDPE and 44 wt. % LLDPE. The sample compositions and initial delamination values determined using the Hydrohead Test are shown in Table 7.

TABLE 7

Delamination results using acrylic acid as the polar co-monomer.

| EX. | Tie-Layer | Initial (kPa) |
|---|---|---|
| 10A | 100% EMA | 2.1 |
| 10B | 100% EAA | 3.5 |
| 10C | 95% EAA + 5% Tack-5 | N.T.* |
| 10D | 95% EAA + 5% Tack-3 | 4.9 |
| 10E | 95% EAA + 5% Tack-4 | 4.1 |

*Not tested. Very poor adhesion.

In some embodiments of the present disclosure, the tie layer may include a polymer including reactive species. The following examples were prepared by blending EMA with various functional polymers having maleic anhydride reactive groups either copolymerized with ("RxCMA") or grafted to ("RxGMA") an olefin-based polymer. All samples were processed at approximately 204° C. The adhesion was measured using the Hydrohead Test and the initial delamination values are reported in Table 8. The results for EX-9A (100% EMA) are repeated here for reference.

TABLE 8

Initial delamination values based on the Hydrohead Test.

| EX- | EMA (wt. %) | Reactive Polymer Type | wt. % | Initial (kPa) |
|---|---|---|---|---|
| 9A | 100 | none | | 4.6 |
| 11A | 90 | RxGMA-1 | 10% | 5.6 |
| 11B | 80 | RxGMA-1 | 20% | 3.2 |
| 11C | 90 | RxGMA-2 | 10% | 7.8 |
| 11D | 80 | RxGMA-2 | 20% | 3.2 |
| 11E | 90 | RxGMA-3 | 10% | 10.6 |
| 11F | 80 | RxGMA-3 | 20% | 10.8 |
| 11G | 99 | RxCMA-1 | 1% | 14.4 |
| 11H | 98 | RxCMA-1 | 2% | 11.0 |
| 11I | 99 | RxCMA-2 | 1% | 18.6 |
| 11J | 98 | RxCMA-2 | 2% | 18.8 |

Additional examples were prepared using a tackified tie layer. Reactivity was introduced using an anyhydride-modified ethylene-methyl acrylate copolymer. In these examples, a two-ply, surfactant-treated, hydrophilic, PLA-based nonwoven was extrusion coated with a two layer, construction using two single screw extruders with single flight screws, a CLOEREN feedblock, and a drop die. The PLA-based web was made hydrophilic with the addition of surfactant to the sheath of the fiber in both layers. The sheath of the fiber made up approximately 32% by volume of the fibers. The sheath contained 1.5 wt. % PEG-5 Cocamide, 1.5 wt. % DOSS, 2 wt. % PP, and 95 wt. % PLA-1 (all % wt). The core of the fibers made up approximately 68% by volume of the fibers and contained only PLA-1 and 0.75 to 1.0 wt. % Blue MB1. The tie layer consisted of the a pre-compounded blend of 90 wt. % EMA and 10 wt. % Tack-1 to which varying amounts of reactive polymer were added. The barrier layer consisted of a blend of LDPE, LLDPE, and blue pigment compounded into LDPE. The processing temperature for both layers was between 202° C. and 210° C. in all instances. The two-layer coating had a total thickness of between 18 microns (0.7 mils) and 28 microns (1.1 mils). The layers were coated at approximately a 1:3 ratio of tie layer to barrier film.

Adhesion was measured using the Hydrohead Test with the pressure set to increase at a rate of 6 kPa/min over a 100 square centimeter circle with the barrier film side up. The failure values for non-sterile and Ethylene Oxide sterilized samples, are summarized in Table 9.

TABLE 9

Failure pressure based on the Hydrohead Test for unsterilized and sterilized samples.

| EX- | (90:10 EMA:Tack-1) (wt. %) | Reactive Polymer Type | wt. % | Failure (kPa) Unsterilized | Sterilized |
|---|---|---|---|---|---|
| REF. | 50 | EMA* | 50% | 11.3 | 6.7 |
| 11A | 90 | RxAH-1 | 10% | 11.4 | 11.0 |
| 11B | 80 | RxAH-1 | 20% | 10.6 | 7.9 |
| 11C | 70 | RxAH-1 | 30% | 11.0 | 8.9 |
| 11D | 90 | RxAH-2 | 10% | 12.1 | 8.8 |
| 11E | 80 | RxAH-2 | 20% | 12.7 | 6.2 |
| 11F | 70 | RxAH-2 | 30% | 9.3 | 4.6 |

*EMA is not a reactive polymer. Included for reference purposes.

Various ethylene-vinyl acetate copolymers (EVA) were evaluated as potential tie-layers for bonding a surfactant-treated, hydrophilic, PLA-based spunbond web to an adjacent polyethylene-based barrier layer. These samples were evaluated qualitatively on a pass/fail basis for adhesion and "hand" of the fabric.

A hydrophilic, PLA-based, spunbond web similar to that referenced in Example 9 was extrusion coated with a 3-layer structure. The EVA-based tie-layer (Layer-B) was adjacent the spunbond PLA web. The barrier layer (Layer A) was positioned between the tie-layer and a surface layer (Layer C). The barrier layer (Layer A) consisted of a blend of 44.5 wt. % LDPE, 44.5 wt. % LLDPE, and 11.0 wt. % Blue MB2 and provided the bulk of the three-layer structure. The surface layer (Layer C) consisted of a blend of 44.5 wt. % LDPE, a 44.5 wt. % polyolefin plastomer (AFFINITY EG8185 available from Dow Chemical Company), and 11.0 wt. % Blue MB2. Layer C provided the exposed surface of the multi-layer article with a desirable coefficient of friction. The layers were coated at a 1:5:1 ratio B:A:C.

Samples prepared with EVA having a vinyl acetate content of 20 wt. % (EVA-20), 25 wt. % (EVA-25) and 28 wt. % (EVA-28a and 28b) showed poor adhesion. Acceptable adhesion was obtained when the vinyl acetate content was increased to 33 wt. % (EVA-33).

An EVA copolymer with 45% wt vinyl acetate content (EVA-45) was also evaluated using the same procedure. In this example, the PLA-based web was made hydrophilic with the addition of surfactant to the sheath of the fiber in both layers. The sheath of the fiber made up approximately 32% by volume of the fibers. The sheath contained 1.5% PEG-5 Cocamide, 1.5 wt. % DOSS, 2 wt. % PP, and 95 wt. % PLA-1. The core of the fibers made up approximately 68% by volume of the fibers and contained only PLA-1 and a blend containing blue pigment.

Adhesion for the EVA-45 based tie layer was measured using the Hydrohead Test. The initial delamination commenced at an average value of 15.1 kPa, with failure at 16.1 kPa. This polymer with a high level of polar vinyl acetate monomer (45%) bonded much better than those polymers with lower VA content, particularly those having a vinyl acetate content of less than 30 percent by weight.

Tie layers were prepared by combining various amounts of a C12-C15 alkyl benzoate plasticizer to an ethylene-methyl acrylate copolymer (EMA). In these examples, a two-ply, surfactant-treated, hydrophilic, PLA-based nonwoven was extrusion coated with a two layer, construction using two single screw extruders with single flight screws, a CLOEREN feedblock, and a drop die. The PLA-based web was made hydrophilic with the addition of surfactant to the sheath of the fiber in both layers. The sheath of the fiber made up approximately 32% by volume of the fibers. The sheath contained 1.5 wt. % PEG-5 Cocamide, 1.5 wt. % DOSS, 2 wt. % PP, and 95 wt. % PLA-1 (all % wt). The core of the fibers made up approximately 68% by volume of the fibers and contained only PLA-1 and 0.75 to 1.0 wt. % Blue MB1. The barrier layer consisted of a blend of LDPE, LLDPE, and blue pigment compounded into LDPE. The processing temperature for both layers was between 202° C. and 210° C. in all instances. The two-layer coating had a total thickness of between 18 microns (0.7 mils) and 28 microns (1.1 mils). The layers were coated at approximately a 1:3 ratio of tie layer to barrier film. The Hydrohead Test was performed before and after sterilization. The results are summarized in Table 10.

TABLE 10

Effects of plasticizer in the tie layer on the failure pressure based on the Hydrohead Test.

| EX- | Plasticizer wt. % | Failure (kPa) Unsterilized | Failure (kPa) Sterilized |
|---|---|---|---|
| REF. | 0% | 40 ± 11 | 2 ± 1 |
| 12A | 10% | 26 ± 4 | 1.4 ± 0.4 |
| 12B | 20% | 20 ± 1 | 1.2 ± 0.3 |
| 12C | 20% | 21 ± 2 | 1.2 ± 0.2 |

In some embodiments, tie layer performance can be improved by blending additional polymers in to the composition. For examples, the present inventors discovered that the inclusion of a thermoplastic elastomer can result in improved adhesion. Suitable thermoplastic elastomers include diblock and triblock copolymers. Exemplary block copolymers include those based on alkyl acrylate and alkyl methacrylate block. In some embodiments, the alkyl methacrylate is methyl methacrylate. In some embodiments, the alkyl acraylte is butyl acraylate. In some embodiments, the thermoplastic elastomer is a polymethacrylate-polyacrylate-polymethacrylate triblock copolymer, e.g., poly(methyl methacrylate)-poly(butyl acrylate)-poly(methyl methacrylate) copolymer. Suitable thermoplastic elastomers include those available from Kurary America under the trade name KURARITY.

Tie layers were prepared by blending a PMMA-PBA-PMMA block copolymer with an ethylene-methyl acrylate copolymer (EMA). Additional tie layers were prepared by adding plasticizer to the block copolymer/EMA blends. The nonwoven multilayer articles were prepared as described for Examples 12A-C. The Hydrohead Test was performed before and after sterilization. The results are summarized in Table 11.

TABLE 11

Failure pressure based on the Hydrohead Test.

| EX- | EMA wt. % | PMMA-PBA-PMMA wt. % | Plasticizer wt. % | Failure (kPa) Unsterilized | Failure (kPa) Sterilized |
|---|---|---|---|---|---|
| REF. | 100% | 0% | 0% | 36 ± 6 | 2.0 ± 0.3 |
| 13A | 75% | 25% | 0% | 70 ± 10 | 14 ± 1 |
| 13B | 25% | 75% | 0% | 230 ± 20 | 200 ± 25 |
| 13C | 67.5 | 22.5% | 10% | 51 ± 7 | 17 ± 2 |
| 13D | 67.5 | 22.5% | 10% | 40 ± 4 | 10 ± 2 |
| 13E | 22.5 | 67.5% | 10% | 21 ± 4 | 7 ± 3 |
| 13F | 22.5 | 67.5% | 10% | 28 ± 8 | 7 ± 4 |
| 13G | 60% | 20% | 20% | 24 ± 4 | 9 ± 1 |

The multi-layer articles of the present disclosure may be used in a wide variety of application. In some embodiments, these articles may be used in medical applications, including those requiring sterilization. Exemplary articles include drapes, gowns, warming blankets, and the like.

Various modifications and alterations of this invention will become apparent to those skilled in the art without departing from the scope and spirit of this invention.

What is claimed is:

1. A multilayer article comprising:
a hydrophilic absorbent layer;
a polyolefin barrier layer; and
a tie layer bonding the absorbent layer to the barrier layer;
wherein the tie layer comprises a thermoplastic composition comprising a copolymer of at least one olefin monomer and at least one polar monomer and/or a block copolymer comprising alkyl methacrylate and alkyl acrylate blocks;
wherein the absorbent layer comprises a nonwoven web of fibers comprising an aliphatic thermoplastic polyester combined with an anionic surfactant and/or a nonionic polyethoxylated surfactant.

2. The multilayer article of claim 1, wherein the tie layer thermoplastic composition comprises a copolymer of at least one olefin monomer and at least one polar monomer.

3. The multilayer article of claim 2, wherein the copolymer of at least one olefin monomer and at least one polar monomer further comprises at least one reactive monomer, wherein the reactive monomer comprises a reactive group that covalently reacts with a hydroxyl group.

4. The multilayer article of claim 2, wherein the tie layer thermoplastic composition further comprises a reactive polymer comprising at least one reactive monomer, wherein the reactive monomer comprises a reactive group that covalently reacts with a hydroxyl group.

5. The multilayer article according to claim 2, wherein at least one olefin monomer is ethylene.

6. The multilayer article according to claim 2, wherein at least one polar monomer is selected from the group consisting of vinyl acetate, a C1 to C8 acrylate, a C1 to C4 acrylic acid, and combinations thereof.

7. The multilayer article according to claim 3, wherein the reactive group of the reactive monomer is an anhydride group or an epoxy group.

8. The multilayer article according to claim 1, wherein the tie layer further comprises a tackifier.

9. The multilayer article according to claim 1, wherein the surfactant comprises an anionic surfactant.

10. The multilayer article according to claim 1, wherein the thermoplastic composition comprises a block copolymer comprising alkyl methacrylate and alkyl acrylate blocks.

11. The multilayer article according to claim 10, wherein the block copolymer is a poly(methyl methacrylate)-poly(butyl acrylate)-poly(methyl methacrylate) copolymer.

12. The multilayer article of claim 1, wherein the tie layer further comprises an alkyl benzoate plasticizer.

13. The multilayer article according to claim 1, wherein the surfactant comprises a nonionic polyethoxylated surfactant.

14. The multilayer article according to claim 13, wherein the nonionic polyethoxylated surfactant is liquid at room temperature.

15. The multilayer article according to claim 1, wherein the surfactant comprises an anionic surfactant and a nonionic polyethoxylated surfactant.

16. The multilayer article according to claim 1, wherein the hydrophilic absorbent layer is formed by combining an aliphatic thermoplastic polyester and a surfactant predissolved in a non-volatile carrier.

17. The multilayer article according to claim 1, wherein the polyolefin barrier layer comprises a low density polyethylene (LDPE), linear low density polyethylene (LLDPE), metallocene polyethylene, polypropylene (PP), or a metallocene polypropylene.

18. The multilayer article according to claim 1, wherein the aliphatic thermoplastic polyester comprises poly(lactic acid), poly(glycolic acid), poly(lactic-co-glycolic acid), polyhydroxybutyrate, polyhydroxyvalerate, blends, or copolymers thereof.

19. A multilayer article comprising:
- an absorbent layer comprising a hydrophilic first ply and a second ply;
- a polyolefin barrier layer which is indirectly bonded to the second ply; and
- a tie layer positioned between and extrusion bonded to the barrier layer and the second ply, wherein the tie layer comprises a thermoplastic composition comprising a copolymer of at least one olefin monomer and at least one polar monomer and/or a block copolymer comprising alkyl methacrylate and alkyl acrylate blocks;
- wherein the first ply comprises a first nonwoven web of fibers comprising an aliphatic polyester combined with an anionic surfactant and/or a nonionic polyethoxylated surfactant, and the second ply comprises a second nonwoven web of fibers comprising the aliphatic polyester.

20. The multilayer article of claim 19, wherein the tie layer thermoplastic composition comprises a copolymer of at least one olefin monomer and at least one polar monomer.

21. The multilayer article of claim 20, wherein the copolymer of at least one olefin monomer and at least one polar monomer further comprises at least one reactive monomer, wherein the reactive monomer comprises a reactive group that covalently reacts with a hydroxyl group.

22. The multilayer article according to claim 20 wherein at least one olefin monomer is ethylene.

23. The multilayer article according to claim 20, wherein at least one polar monomer is selected from the group consisting of vinyl acetate, a C1 to C8 acrylate, a C1 to C4 acrylic acid, and combinations thereof.

24. The multilayer article according to claim 21, wherein the reactive group of the reactive monomer is an anhydride group or an epoxy group.

* * * * *

UNITED STATES PATENT AND TRADEMARK OFFICE
CERTIFICATE OF CORRECTION

| | |
|---|---|
| PATENT NO. | : 10,098,980 B2 |
| APPLICATION NO. | : 14/433884 |
| DATED | : October 16, 2018 |
| INVENTOR(S) | : Karls et al. |

It is certified that error appears in the above-identified patent and that said Letters Patent is hereby corrected as shown below:

In the Specification

Column 3
Lines 8-9, Delete "polybutylene" and insert -- poly(butylene --, therefor.

Column 4
Lines 51-52, Delete "polalkoxylate" and insert -- polyalkoxylate --, therefor.

Column 6
Line 54, Delete "(mm)" and insert -- (mm). --, therefor.

Column 9
Lines 34-35, Delete "LOTADUR" and insert -- LOTADER --, therefor.
Line 35, Delete "LOTADUR" and insert -- LOTADER --, therefor.
Line 37, Delete "glycidylmethyacrylate" and insert -- glycidylmethacrylate --, therefor.

Columns 13-14
Line 39 (Table 1), Delete "Anyhydride" and insert -- Anhydride --, therefor.
Line 41 (Table 1), Delete "Anyhydride" and insert -- Anhydride --, therefor.

Column 19
Line 19, Delete "anyhydride-" and insert -- anhydride- --, therefor.
Line 32 (Approx.), Delete "the a" and insert -- the --, therefor.

Column 21
Line 22 (Approx.), Delete "acraylte" and insert -- acrylate --, therefor.
Line 27 (Approx.), Delete "Kurary" and insert -- Kuraray --, therefor.

Signed and Sealed this
Fourteenth Day of May, 2019

Andrei Iancu
*Director of the United States Patent and Trademark Office*